United States Patent
Potyrailo et al.

(10) Patent No.: US 6,193,850 B1
(45) Date of Patent: Feb. 27, 2001

(54) METHOD FOR DIRECT MEASUREMENT OF POLYCARBONATE COMPOSITIONS BY FLUORESCENCE

(75) Inventors: Radislav Alexandrovich Potyrailo, Niskayuna; John Patrick Lemmon, Delanson, both of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/398,678

(22) Filed: Sep. 20, 1999

(51) Int. Cl.[7] .................. G01N 23/22; C09K 11/02; C08G 64/04; C08G 64/16
(52) U.S. Cl. ............ 204/157.15; 250/306; 250/459.1; 250/462.1; 252/301.19; 252/301.35; 522/163; 522/183; 524/841; 528/196; 528/370; 528/372
(58) Field of Search ................. 522/2, 163, 183; 528/196, 370, 372; 204/157.15; 524/841; 356/317, 417; 250/306, 307, 459.1, 461.1, 462.1; 252/301.16, 301.19, 301.35

(56) References Cited

U.S. PATENT DOCUMENTS

| | | | |
|---|---|---|---|
| 4,371,660 | * | 2/1983 | Calundann et al. . |
| 4,577,110 | * | 3/1986 | MacBride et al. . |
| 4,749,726 | * | 6/1988 | Gupta et al. . |
| 4,918,149 | * | 4/1990 | Clagett et al. . |
| 5,100,802 | * | 3/1992 | Mickols . |
| 5,151,748 | * | 9/1992 | Bur et al. . |
| 5,489,536 | * | 2/1996 | Ekechukwu et al. . |
| 5,608,026 | * | 3/1997 | Hoover et al. . |
| 5,633,504 | * | 5/1997 | Collins et al. . |
| 5,872,275 | * | 2/1999 | Komiya et al. . |

OTHER PUBLICATIONS

Spatially resolved analyte mapping with time–of–flight optical sensors, Radislav A. Potyrailo and Gary M. Hieftje, Trends in Analytical Chemistry, vol. 17, No. 10, 1998, pp. 593–604.

* cited by examiner

Primary Examiner—Susan W. Berman
(74) Attorney, Agent, or Firm—Noreen C. Johnson; Douglas E. Stoner (57) ABSTRACT

The present invention provides a method for directly determining the concentration of a target species, such as Fries product, in a composition comprising aromatic carbonate chain units. In an exemplary embodiment, the method includes the steps of irradiating a portion of the composition with electromagnetic radiation at an excitation wavelength sufficient to cause the target species to emit a fluorescence spectrum; detecting at least a portion of the fluorescence spectrum; and determining the concentration of the target species from the fluorescence spectrum. In addition to detecting Fries product in formed polycarbonate materials, the method can also be utilized to directly determine the concentration of a target species in parallel polycarbonate reactor systems.

30 Claims, 11 Drawing Sheets

METHOD FOR DIRECT MEASUREMENT OF POLYCARBONATE COMPOSITIONS BY FLUORESCENCE

BACKGROUND OF THE INVENTION

1. Field of the Invention

The present invention relates to a method for direct measurement of fluorescent products in polycarbonate compositions and, more specifically, to a method for rapid direct quantification of thermal Fries product in the products of melt polycarbonate reactions.

2. Discussion of Related Art

Conventional industrial plants synthesize polycarbonate by mixing together an aqueous solution of a dihydroxy compound (e.g., bisphenol-A) with an organic solvent (e.g., dicloromethane) containing a carbonyl halide (e.g., phosgene). Upon mixing the immiscible organic and aqueous phases, the dihydroxy compound reacts with the carbonyl halide at the phase interface. Typically, a phase transfer catalyst, such as a tertiary amine, is added to the aqueous phase to enhance the reaction. This synthesis method is commonly known as the "interfacial" synthesis method for preparing polycarbonates, and the product of this synthesis is commonly known as LF grade polycarbonate.

The interfacial method for making polycarbonate has several inherent disadvantages. First, it can be a disadvantage to operate a process that requires phosgene as a reactant. Second, the process utilizes large amounts of an organic solvent, which can require expensive precautionary measures to prevent deleterious environmental effects. Third, the interfacial method requires significant capital investment in equipment. Fourth, polycarbonate produced by the interfacial process is prone to exhibiting inconsistent color, high levels of particulates, and high chloride concentration.

An alternate polycarbonate manufacturing method has been developed which avoids several of the aforementioned problems. This synthesis technique, commonly referred to as the "melt" process, involves the transesterification of a carbonate diester (e.g., diphenylcarbonate) with a dihydroxy compound (e.g., bisphenol-A). This reaction is typically performed without a solvent and is driven to completion by mixing the reactants under reduced pressure and high temperature with simultaneous distillation of the phenol produced by the reaction. Polycarbonate produced by the melt process is typically referred to as LX grade polycarbonate. The melt process provides many advantages over the interfacial process. More specifically, the melt process does not employ phosgene; it does not require a solvent; and it uses less equipment. Moreover, the polycarbonate produced by the melt process does not contain chlorine contamination from the reactants; it has lower particulate levels; and it has a more consistent color. Therefore, in certain circumstances, it can be highly desirable to use the melt process in production facilities.

However, the melt process tends to produce polycarbonate with significantly higher level of branching than that produced by the interfacial process. This branching is the result of a side reaction called the Fries rearrangement, which involves the conversion of a phenolic ester into corresponding ortho and para hydroxyketones. The rearrangement is based on the Fries rule, which postulates that the most stable form of a polynuclear compound is that arrangement which has the maximum number of rings in the benzenoid form.

The Fries rearrangement product in polycarbonate is typically the result of exposure to elevated temperatures in the presence of an active catalyst. The primary Fries product is a salicylate ester that, under melt polymerization conditions, can further react to form a tri-functional molecule that acts as a branch point for the resulting polymer. In this context, the generation of the Fries branch point structure can lead to polymer branching, thereby generating inconsistent melt behavior. In various applications, this branching significantly increases the ductility of the polycarbonate and is, therefore, undesirable.

As the demand for high performance materials has continued to grow, new and improved methods of providing improved products more economically are needed to supply the market. Due in part to the advantages inherent in polycarbonate production by the melt process, there is significant interest among industry members in producing LX grade polycarbonate with low Fries product content. In this context, various reactant and catalyst combinations for melt polymerization are constantly being evaluated; however, the identities of chemically or economically superior reactant systems for melt polymerization processes continue to elude the industry. As parallel screening gains popularity in all areas of chemistry, high-throughput screening of potential reactant systems will become increasingly important. As such, new and improved methods are needed for rapid, direct quantification of reaction products.

SUMMARY

Accordingly, the present invention is directed to a method for directly determining the concentration of a target species, such as Fries product, in a composition comprising aromatic carbonate chain units. In an exemplary embodiment, the method of the present invention includes the steps of irradiating a portion of the composition with electromagnetic radiation at an excitation wavelength sufficient to cause the target species to emit a fluorescence spectrum; detecting at least a portion of the fluorescence spectrum; and determining the concentration of the target species from the fluorescence spectrum. Optionally, two or more spectra can be obtained, each containing a second order Rayleigh scatter peak. The spectra can be scaled such that the second order Rayleigh scatter peaks are the same height before determining the concentration of the target species. In addition to detecting Fries product in formed polycarbonate materials, the method can also be utilized to directly determine the concentration of a target species in parallel polycarbonate reactor systems.

BRIEF DESCRIPTION OF THE DRAWINGS

Various features, aspects, and advantages of the present invention will become more apparent with reference to the following description, appended claims, and accompanying drawings, wherein

DETAILED DESCRIPTION

Terms used herein are employed in their accepted sense or are defined. In this context, the present invention is directed to a method for directly determining the concentration of a target species in a composition comprising aromatic carbonate chain units. It is contemplated that such a composition may be the product of a melt polymerization reaction or an interfacial polymerization reaction. The method may be performed during a reaction or upon the final product of the reaction. It is further contemplated that the method can be performed on polycarbonate compositions that have been subjected to further processing. The method is capable of determining the concentration of a target species, such as Fries product or the like, by direct fluorescence measurements. The direct analytical method can be performed on polycarbonate compositions in various forms including, for example, films, pellets, sheets, solutions, suspensions, or blends containing polycarbonate.

In various embodiments, the disclosed method eliminates the need for extensive sample preparation as required by other detection methods. For example, polycarbonate depolymerization followed by liquid chromatography analysis requires a time consuming (30–60 minutes) sample preparation step involving dissolution of the polycarbonate. Likewise, it can take 2 hours or more to complete a single measurement using NMR methodology, thereby effectively eliminating the opportunity to quantify a target species in real time during a reaction or in connection with parallel combinatorial screening.

As used herein, the terms "polycarbonate", "polycarbonate composition", and "composition comprising aromatic carbonate chain units" includes compositions having structural units of the formula (I):

(I)

in which at least about 60 percent of the total number of $R^6$ groups are aromatic organic radicals and the balance thereof are aliphatic, alicyclic, or aromatic radicals. Preferably, $R^6$ is an aromatic organic radical and, more preferably, a radical of the formula (II):

(II)

wherein each of $A^1$ and $A^2$ is a monocyclic divalent aryl radical and $Y^1$ is a bridging radical having one or two atoms which separate $A^1$ from $A^2$. In an exemplary embodiment, one atom separates $A^1$ from $A^2$. Illustrative non-limiting examples of radicals of this type are —O—, —S—, —S(O)— or —S(O$_2$)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ can be a hydrocarbon group or a saturated hydrocarbon group such as methylene, cyclohexylidene or isopropylidene.

Polycarbonates can be derived from dihydroxy compounds in which only one atom separates $A^1$ and $A^2$. As used herein, the term "dihydroxy compound" includes, for example, bisphenol compounds representative of general formula (III) as follows:

(III)

In formula (III), $R^a$ and $R^b$ each represent a halogen atom or a monovalent hydrocarbon group and may be the same or different. The p and q variables represent integers from 0 to 4. The $X^a$ variable represents one of the following groups:

Variables $R^c$ and $R^d$ each independently represent a hydrogen atom or a monovalent hydrocarbon group. Variables $R^c$ and $R^d$ may form a ring structure. Variable $R^e$ is a divalent hydrocarbon group.

Some illustrative, non-limiting examples of suitable dihydroxy compounds include the dihydroxy-substituted aromatic hydrocarbons disclosed by name or formula (generic or specific) in U.S. Pat. No. 4,217,438, which is incorporated herein by reference. A nonexclusive list of specific examples of the types of bisphenol compounds that may be represented by formula (III) includes the following:

1,1-bis(4-hydroxyphenyl) methane;
1,1-bis(4-hydroxyphenyl) ethane;
2,2-bis(4-hydroxyphenyl) propane (hereinafter referred to as "bisphenol A" or "BPA");
2,2-bis(4-hydroxyphenyl) butane;
2,2-bis(4-hydroxyphenyl) octane;
1,1-bis(4-hydroxyphenyl) propane;
1,1-bis(4-hydroxyphenyl) n-butane;
bis(4-hydroxyphenyl) phenylmethane;
2,2-bis(4-hydroxy-1-methylphenyl) propane;
1,1-bis(4-hydroxy-t-butylphenyl) propane;
bis(hydroxyaryl) alkanes such as 2,2-bis(4-hydroxy-3-bromophenyl) propane;
1,1-bis(4-hydroxyphenyl) cyclopentane; and
bis(hydroxyaryl) cycloalkanes such as 1,1-bis(4-hydroxyphenyl) cyclohexane.

Preferred LX polycarbonates are bisphenol A polycarbonates, in which each of $A^1$ and $A^2$ is p-phenylene and $Y^1$ is isopropylidene. Preferably, the average molecular weight of the initial polycarbonate ranges from about 5,000 to about 100,000; more preferably from about 10,000 to about 65,000, and most preferably from about 15,000 to about 35,000.

In monitoring and evaluating polycarbonate synthesis, it is of particular interest to determine the concentration of Fries product present in the polycarbonate. As noted, the generation of significant Fries product can lead to polymer branching, resulting in uncontrollable melt behavior. As used herein, the terms "Fries" and "Fries product" denote a repeating unit in polycarbonate having the following formula:

(IV)

wherein $X^a$ is a bivalent radical as described in connection with Formula (III) supra.

In an exemplary embodiment, the present method is capable of directly determining the concentration of a target species (e.g., Fries product) in a composition comprising aromatic carbonate chain units. The method includes the steps of irradiating a portion of the composition with electromagnetic radiation at an excitation wavelength sufficient to cause the target species to emit a fluorescence spectrum; detecting at least a portion of the fluorescence spectrum; and determining the concentration of the target species from the fluorescence spectrum.

In order to provide adequate quantification of the target species, the composition is preferably irradiated at an excitation wavelength that allows the target species to fluoresce at a detectable level that provides differential emission between the target species and interfering species. The present method permits quantification of Fries product during a melt polymerization reaction in the presence of fluorescent, absorbing, and scattering interfering species. The conditions used allow for selective excitation of the Fries product in the polycarbonate material; collection of its fluorescence emission; and relation of the measured fluorescence signal to Fries concentration. The range of excitation wavelengths for quantification of Fries product is preferably selected to satisfy at least two criteria: (1) appreciable absorbance of the selected excitation wavelengths by Fries product and (2) minimal absorbance of the selected excitation wavelengths by interfering species. The range of emission wavelengths for quantification of Fries product is preferably selected to satisfy at least two criteria: (1) Fries product emits fluorescence and (2) interfering species do not appreciably emit fluorescence.

Figure 1:
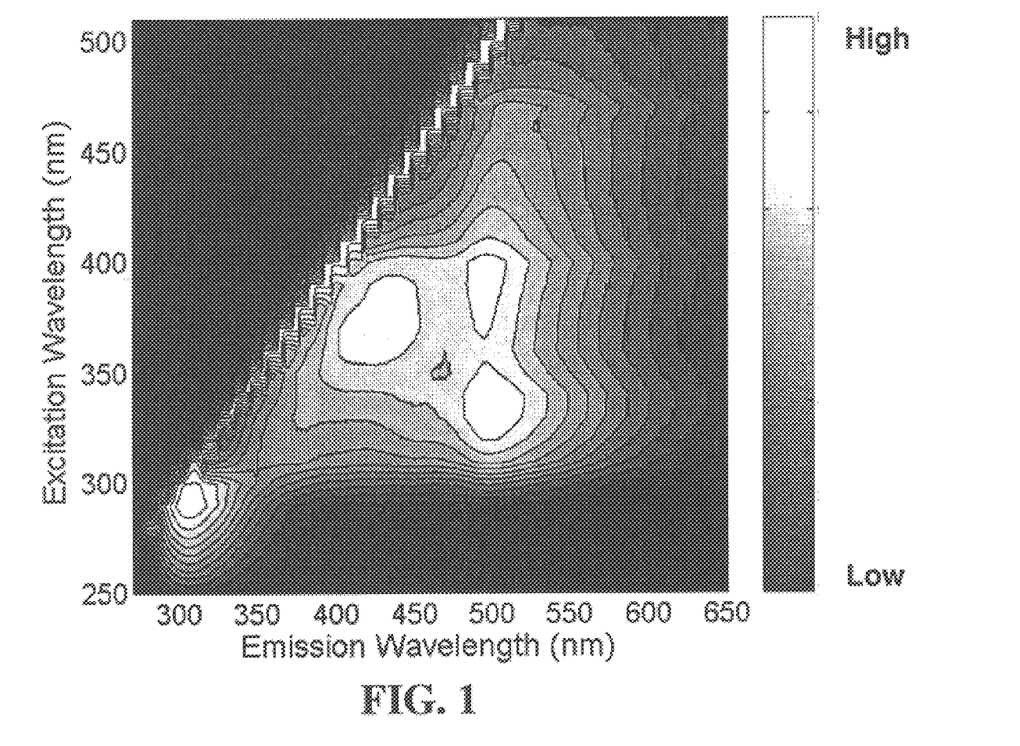
FIG. 1 is an excitation-emission spectrum of solid LX melt polycarbonate.

In addition to Fries product, which produces detectable fluorescence signal, there are several possible interfering species in LX material. Exemplary interfering species include non-branched Fries end-groups, non-Fries end-groups, and cyclics. Also, different contaminant species may potentially emit fluorescence. A typical excitation-emission spectrum of a solid LX material (119 ppm of Fries product) is presented in FIG. 1 to illustrate the complexity of the fluorescence spectrum of a solid LX material obtained after a melt polymerization reaction. When dealing with Fries product as the target species, a suitable excitation wavelength is between about 250 nm and about 500 nm; preferably between about 300 nm and about 400 nm; more preferably between about 320 nm and about 350 nm; and most preferable about 340 nm. Other portions of the excitation and emission fluorescence spectra can be collected for calibration, normalization, and scaling purposes.

Compensation for the variation in absorbance and scattering effects of the measured regions at the excitation and emission wavelengths can be accomplished by at least two compensation methods. The first compensation method comprises measuring the absorption spectrum of the probed region of polycarbonate over the spectral range that covers the excitation and emission wavelengths. The second compensation method comprises using second order Rayleigh scattering effects in the emission and excitation spectra for scaling the spectral features.

In real-time monitoring situations, the collected fluorescence intensity can be affected by a number of instrumental and sample parameters not related to the concentration of the fluorescent product. However, various embodiments of the disclosed method allow for compensation to provide reproducible signals from single or multiple polymerization reactors during monitoring of the progress of, e.g., a polycarbonate melt polymerization reaction.

Figure 2:
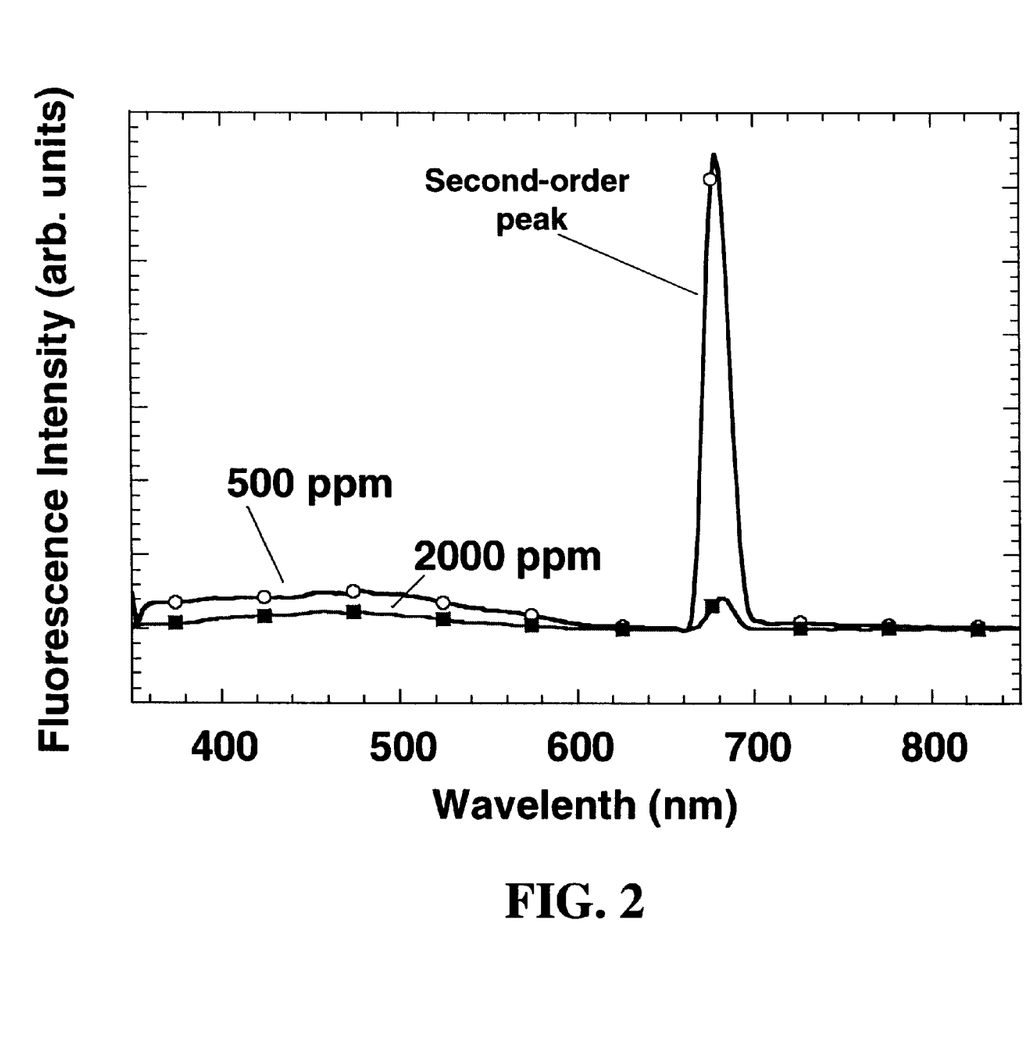
FIG. 2 is a graphical representation of fluorescence spectra of various concentrations of Fries product in polycarbonate.
Figure 3:
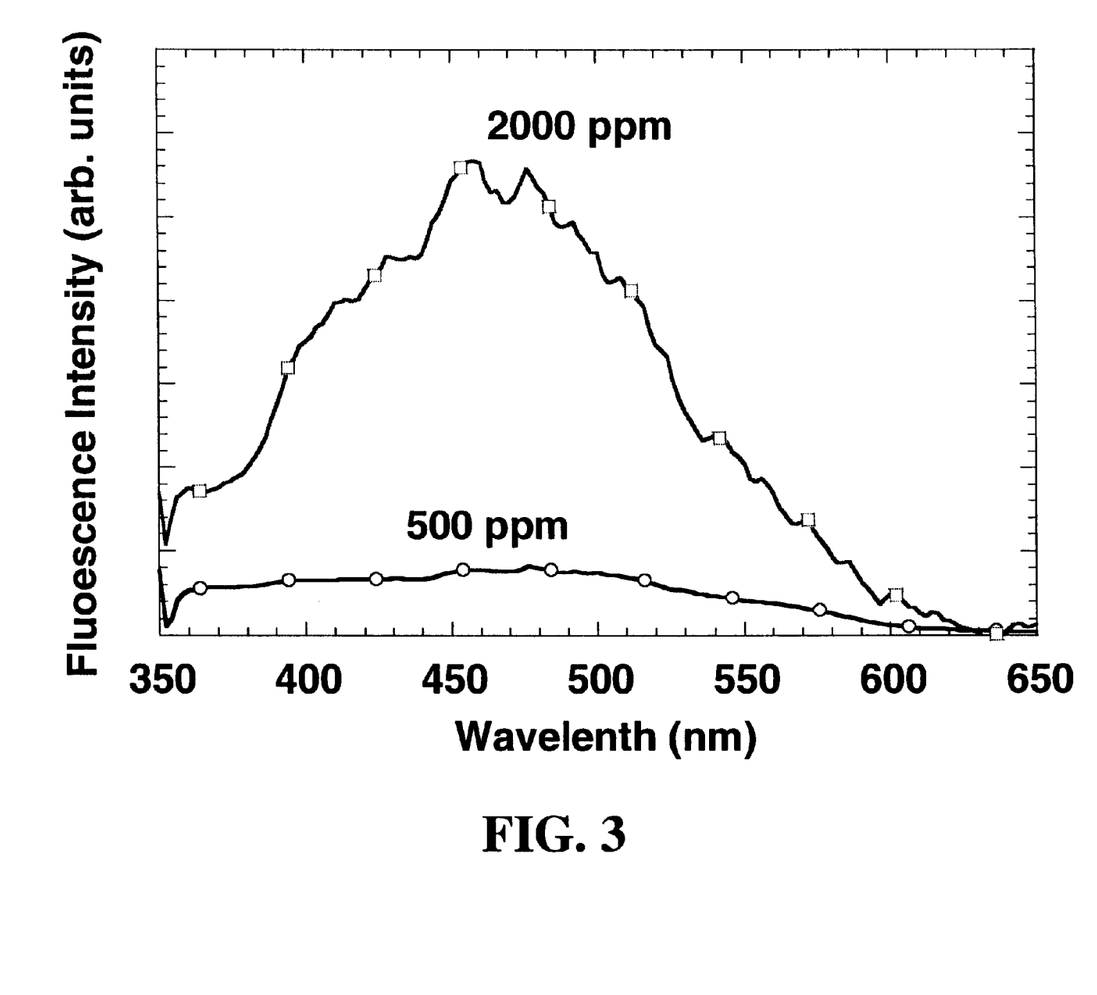
FIG. 3 is a graphical representation of fluorescence spectra of various concentrations of Fries product in polycarbonate.

Second-order Rayleigh scattering effects are typically undesirable in conventional spectrometers for general applications because they distort the true spectral features of the measured samples. These second order effects in the emission and excitation spectra can be eliminated by various techniques. For example, it is common to use excitation and emission filters that block the respective spectral portion of radiation from entering the measurement device (spectrometer). However, in various alternative embodiments of the present method, second order effects are used to scale spectral features. An example of second-order effects is shown in FIG. 2, where the peaks at 680 nm in both recorded spectra of solid polycarbonate samples are second-order effects resulting from excitation at 340 nm. These second order peaks are measured and used as reference excitation intensity. As shown in FIG. 2, the intensities of these peaks are different due to different excitation conditions of the two samples. However, as shown in FIG. 3, after scaling both second-order peaks to the same height, the resulting spectra for two different concentrations of Fries product can be readily compared. In this manner a measurement taken during or after a reaction can be compared to a standard measurement or to a measurement taken earlier in the reaction cycle.

The present method can be used to directly determine the concentration of a target species in parallel polycarbonate reactor systems having multiple reaction zones. In this embodiment, the method includes the steps of disposing an optical probe proximate each of the reaction zones and conducting a melt polymerization reaction within each of the reaction zones such that each zone contains a composition having aromatic carbonate chain units. Electromagnetic radiation is passed through each of the optical probes at an excitation wavelength sufficient to cause the target species to emit a fluorescence spectrum. At least a portion of the fluorescence spectrum is detected from each of the reaction zones in order to determine the concentration of the target species in each zone.

Figure 4:
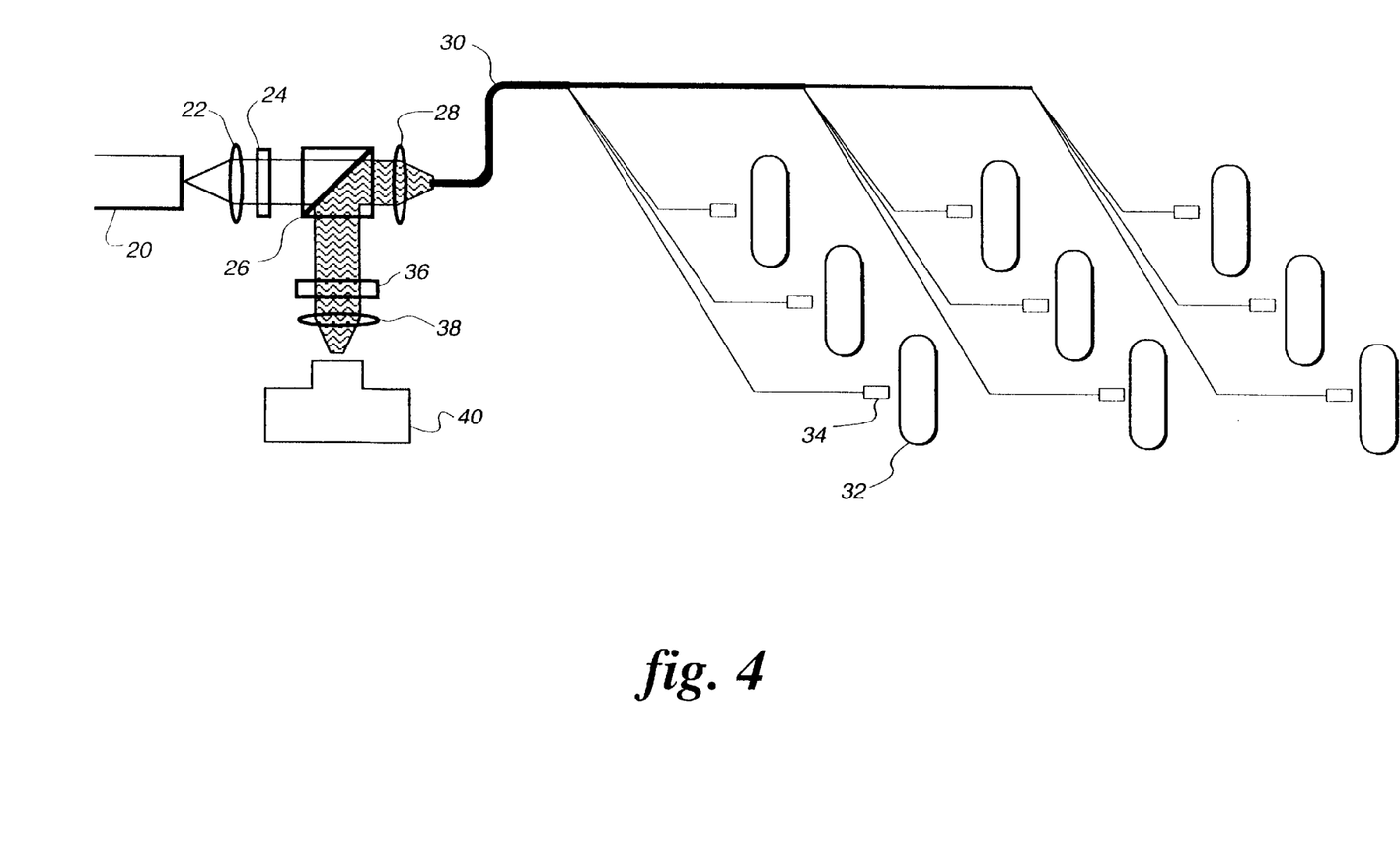
FIG. 4 is a schematic view of an apparatus capable of performing an aspect of an embodiment of the present invention.

An apparatus for parallel monitoring of Fries product in multiple polymerization reactors is presented in FIG. 4. It is contemplated that the apparatus shown can be useful for combinatorial screening of catalysts and the like. The apparatus includes a white light source 20, a collimator 22, an excitation optical filter 24, a beam splitter 26, a focusing lens 28, a fiber optic bundle 30, a plurality of polymerization reactors 32, a plurality of optical probes 34, an emission optical filter 36, a second focusing lens 38, and an imaging photo-detector 40.

Figure 5:
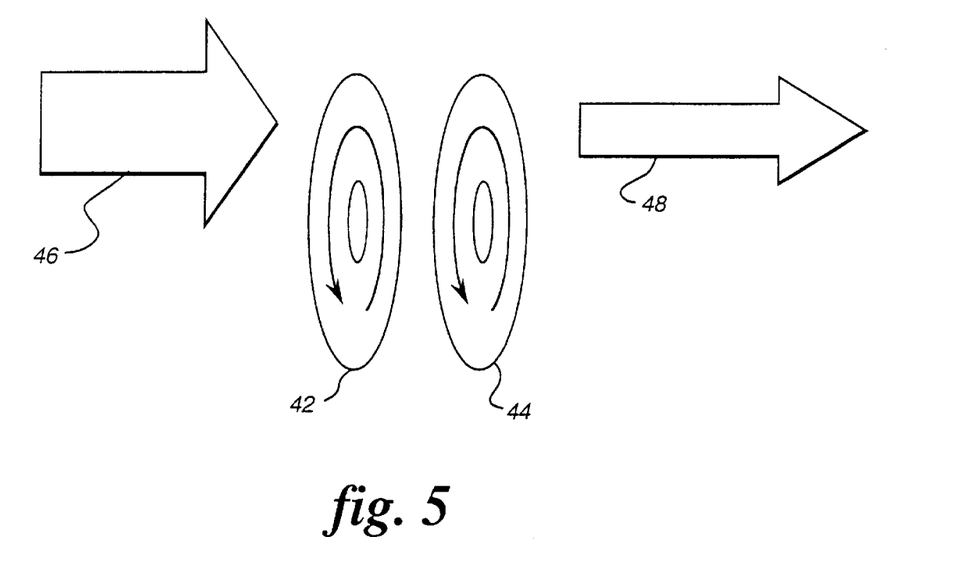
FIG. 5 is a schematic view of a portion of an apparatus capable of performing an aspect of an embodiment of the present invention.

In operation, polymerization reactions are carried out in polymerization reactors 32 to produce polycarbonate. White light from source 20 is collimated and passed through excitation optical filter 24. As shown in FIG. 5, both excitation optical filter 24 and emission optical filter 36 preferably comprise two filter elements 42, 44 with each of the filter elements having a continuous linear variation of either cut-on or cut-off wavelength. Such optical filter elements are commercially available, for example, from Coherent, Inc. of Auburn, Calif. White light 46 can be converted to colored light by using an opposed pair of these filter elements. The bandwidth of white light 46 can be adjusted by counter rotating the elements, while coordinated rotation changes the center wavelength. In this manner, incoming white light 46 can be converted to constant-bandwidth, variable wavelength output light 48.

With reference the FIG. 4, the filtered light passes through beam splitter 26 and is focused onto the tip of fiber-optic bundle 30. The fiber-optic bundle is comprised of individual fibers or sub-bundles arranged together at one end and positioned at each reactor 32 at the other end. Light is delivered to the reaction zone via optical probes 34. Each optical probe can comprise a single optical fiber or a bifurcated fiber-optic bundle. Optionally, because melt polycarbonate in a reaction vessel is a highly absorbing and scattering medium at the excitation and emission wavelengths of Fries products, it may be advantageous to utilize a probe having a central fiber or set of fibers for carrying the excitation light.

Figure 6:
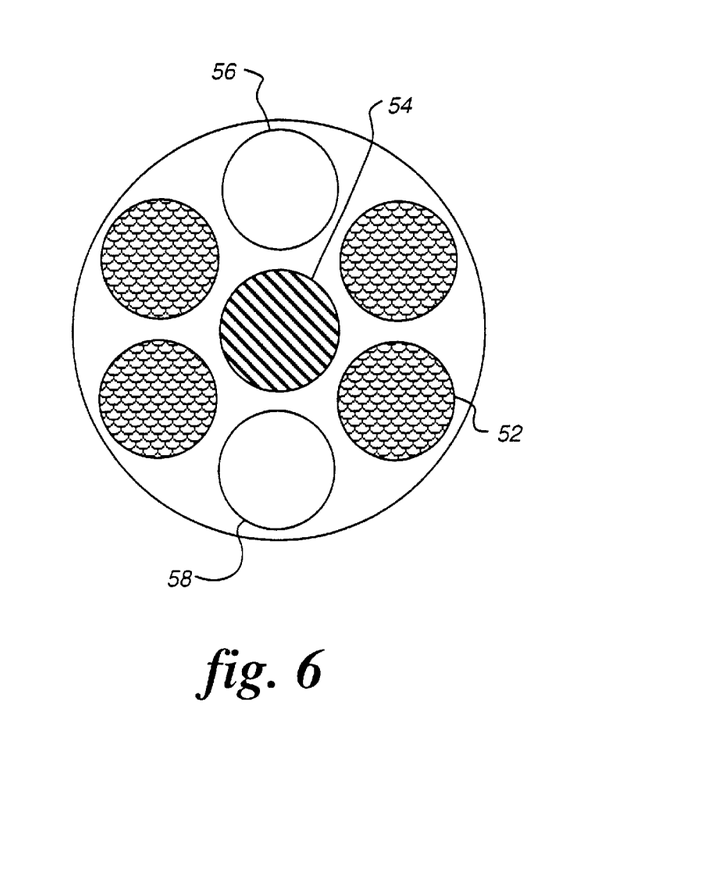
FIG. 6 is a cross-sectional view of a portion of an apparatus capable of performing an aspect of an embodiment of the present invention.

An example of a cross-section of such a probe is shown in FIG. 6 wherein a plurality of collection fibers 52 are disposed around an excitation fiber 54 to collect fluorescence and deliver the same to photo-detector 40 (FIG. 4). A third fiber 56 is used to deliver white light to the measurement location while a fourth fiber 58 is used to deliver the back propagated portion of light to the detector. These absorption/reflection measurements can be used to compensate for variations in fluorescence signal due to the primary and secondary inner filter effects.

As used herein, the term "inner filter effect" includes the significant absorption of the excitation or emission radiation as the radiation travels through the medium where the target species is located. More specifically, "primary inner filter effect" denotes significant absorption of the excitation radiation, and "secondary inner filter effect" denotes significant absorption of the emission radiation. As known to those skilled in the art, inner filter effects can affect the relationship between luminescence signal and analyte concentration, and correction factors can be calculated from absorbance and scatter at the excitation and emission wavelengths in order to compensate for the loss of optical signal at these wavelengths. Use of the probe shown in FIG. 6 can also compensate for variations in the refractive index of the optical medium.

As shown in FIG. 4, light propagating back from each of the measurement locations is directed through beam splitter 26 and emission optical filter 36 having variable edge-pass optical filter elements 42, 44 (FIG. 5) before being focused into imaging photo-detector 40, such as, e.g., a CCD camera or the like. Depending on the relative position of filter elements 42, 44 in each filter, excitation-emission fluorescence matrices can be collected simultaneously from each reactor 32. When excitation optical filter 24 is set to transmit white light, the absorbance/reflectance spectra are collected from each reactor 32 by the coordinated rotation of emission filter elements 42, 44. Imaging photo-detector 40 is used for monitoring the fluorescence or absorbance/reflection changes at each of the multiple measurement locations.

Figure 7:
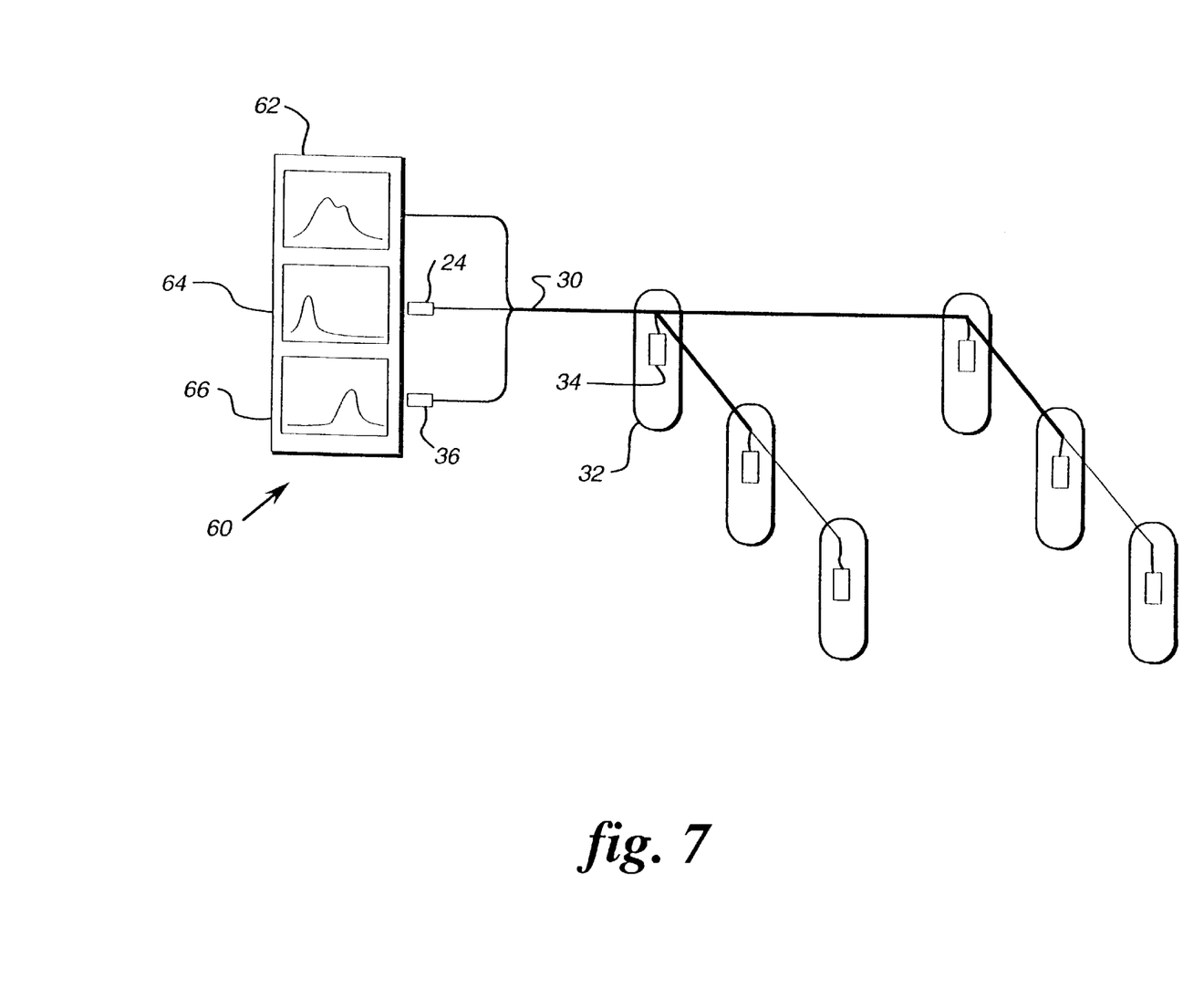
FIG. 7 is a schematic view of an apparatus capable of performing an aspect of an embodiment of the present invention.

Another apparatus for parallel on-line monitoring of Fries product in multiple polymerization reactors is shown in FIG. 7. The apparatus includes a multichannel spectrometer 60 having an absorbance/reflectance channel 62, a fluorescence-excitation channel 64, and a fluorescence-emission channel 66. A fiber-optic bundle 30 is placed in optical communication with spectrometer 60 and a plurality of optical probes 34 (as described above), which can be located proximate reactors 32 (non-invasive) or immersed in reactors 32 (invasive, as shown). Two of the channels 64, 66 are provided with optical filters 24, 36 (described supra).

In operation, multichannel spectrometer 60 is capable of measuring the excitation and emission fluorescence spectra and absorbance/reflectance from each reactor 32 in rapid sequence. Measurements in multiple reactors can be accomplished using the art-recognized time-domain multiplexing approach or having a miniature spectrometer for each of the reactors.

EXAMPLES

The following examples are provided in order that those skilled in the art will be better able to understand and practice the present invention. These examples are intended to serve as illustrations and not as limitations of the present invention as defined in the claims herein.

EXAMPLE 1

Figure 8:
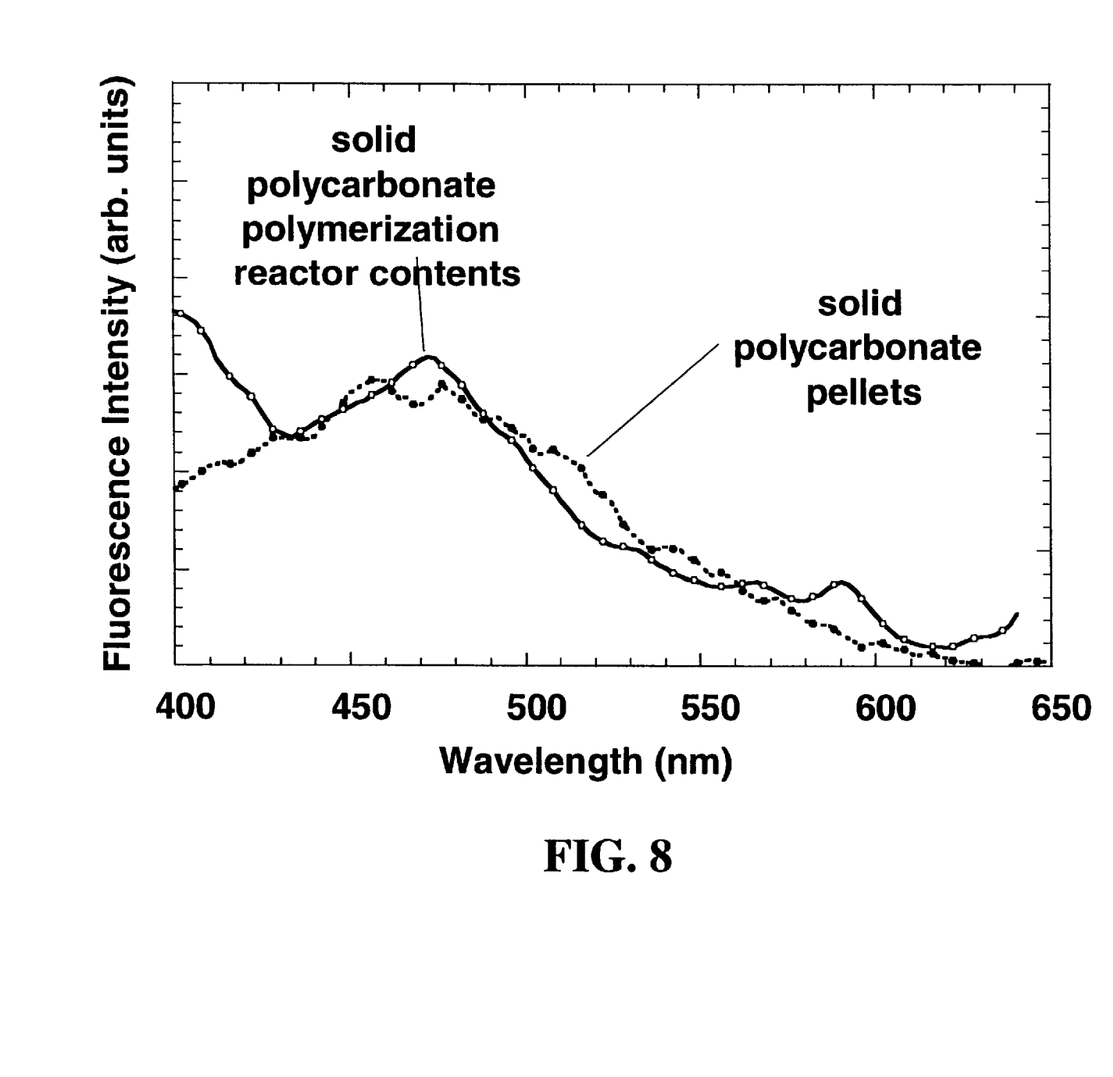
FIG. 8 is a graphical representation comparing fluorescence spectra of solid polycarbonate pellets with the contents of a polymerization reactor.

Solid polycarbonate material was produced through a solventless melt transesterification of diphenylcarbonate with bisphenol-A under reduced pressure and high temperature with simultaneous distillation of the resulting phenol. Measurements of fluorescence spectra of the resulting polycarbonate were performed in situ using the direct measurement method described above before removing the polycarbonate from the polymerization reactor. Fluorescence measurements of processed LX-grade polycarbonate pellets were also taken using the same direct method. The excitation wavelength for all tests was 340 nm. As shown in FIG. 8, close similarity of the fluorescence spectra of polycarbonate pellets and solid polycarbonate material in the polymerization reactor demonstrates the applicability of the present method for direct, in situ measurement of Fries product in polymerization reactors during the production of melt polycarbonate.

EXAMPLE 2

Figure 9:
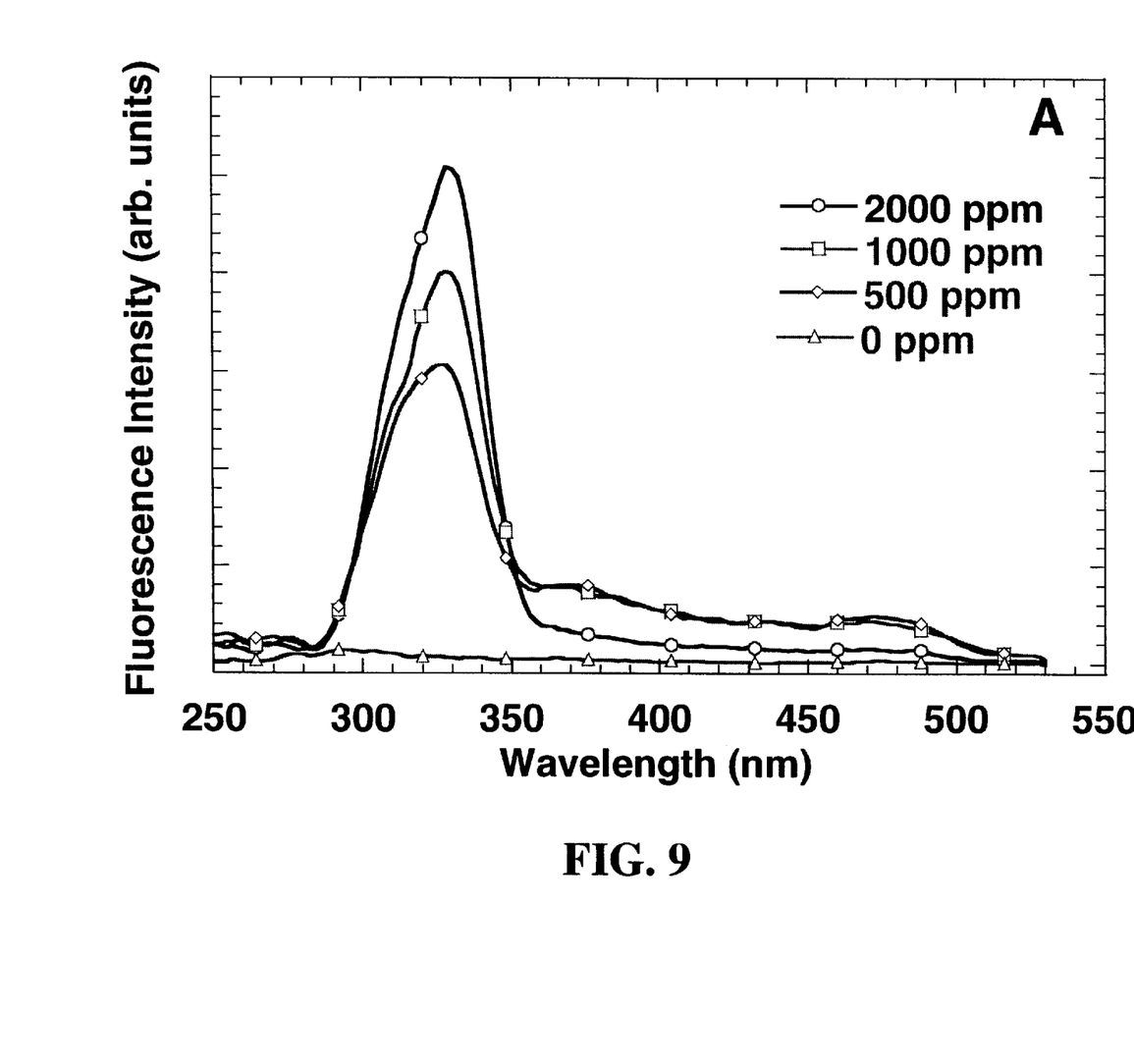
FIG. 9 is a graphical representation of excitation spectra of solutions of LF polycarbonate with varying concentration of Fries product.
Figure 10:
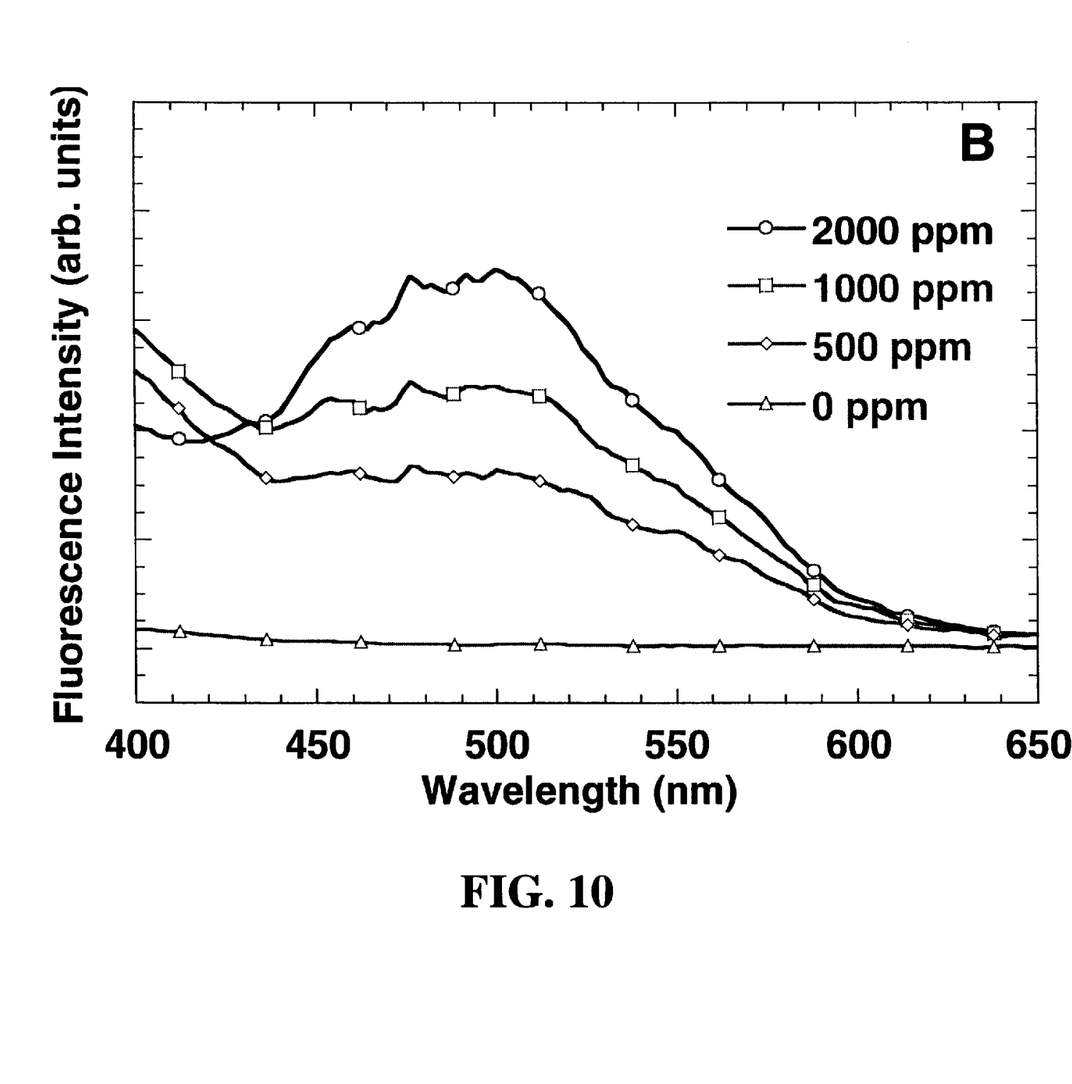
FIG. 10 is a graphical representation of emission spectra of solutions of LF polycarbonate with varying concentration of Fries product.

To determine the efficacy of direct fluorescence detection of Fries product in polycarbonate, measured amounts of Fries product initiator were added to a solution of LF-grade polycarbonate in dichloromethane to produce polycarbonate with predetermined concentrations of Fries product. Fluorescence spectra of the resulting solutions were obtained by using the direct measurement method described above. As shown in FIGS. 9 and 10, varying Fries concentration produced varying spectral features. Emission wavelength for the excitation spectra (FIG. 9) was 550 nm. Excitation wavelength for the emission spectra (FIG. 10) was 340 nm.

Figure 11:
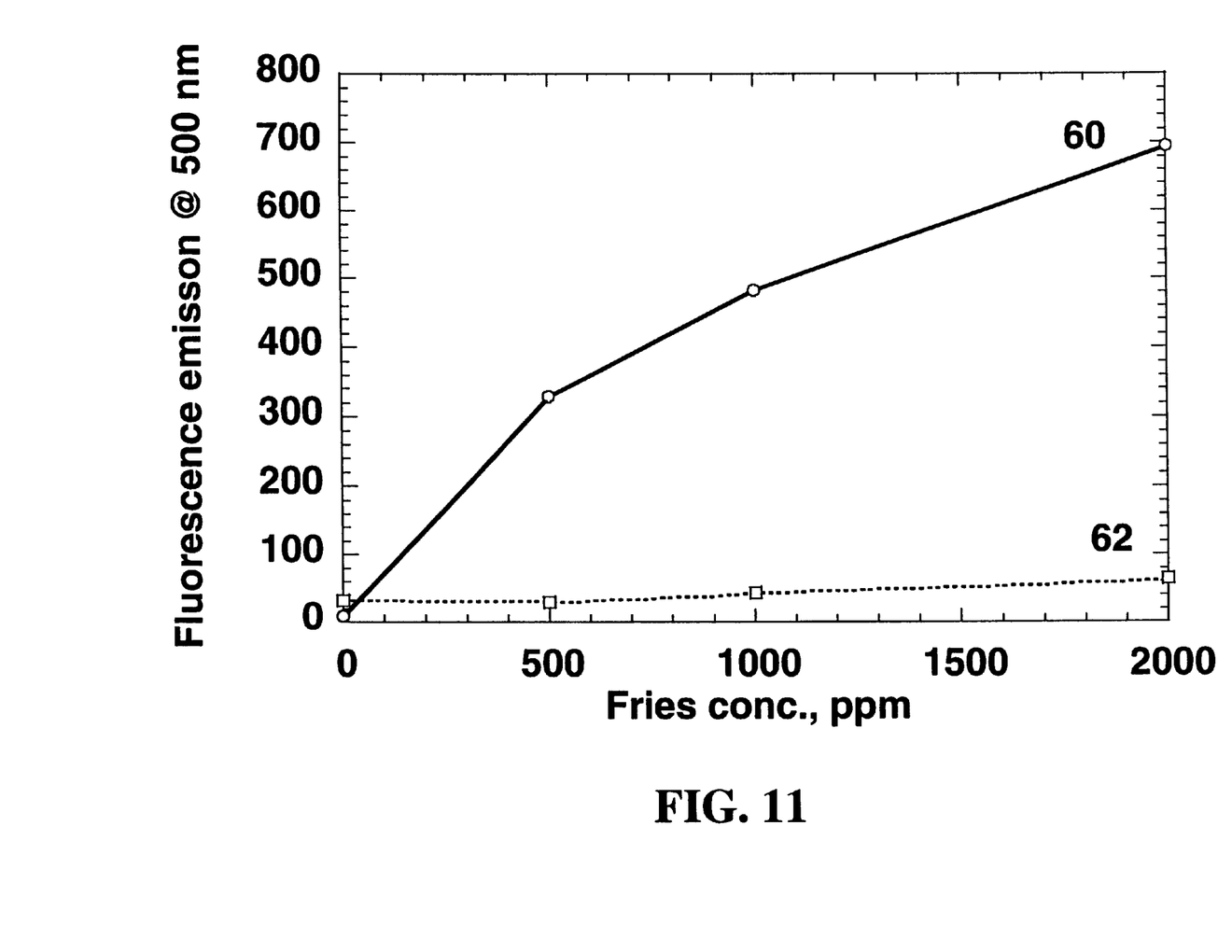
FIG. 11 is a graphical representation of the fluorescence intensities of solutions of LF polycarbonate in dichloromethane as a function of Fries product.

As shown in FIG. 11, measurements of fluorescence emission intensity are also useful for quantification of Fries product. Based on the fluorescence intensity at the lowest measured Fries concentration and the background noise level, the detection limit for Fries determinations was calculated to be 60 ppm (S/N=3) at the conditions utilized.

FIG. 11 also illustrates the significance of the excitation wavelength selection. Curve 60 represents spectra obtained at an excitation wavelength of 340 nm. Curve 62 represents spectra obtained at an excitation wavelength of 320 nm. Although the optimum excitation wavelength can vary depending on conditions encountered, under the conditions used, there was a significant change in fluorescence signal between 320 and 340 nm.

Figure 12:
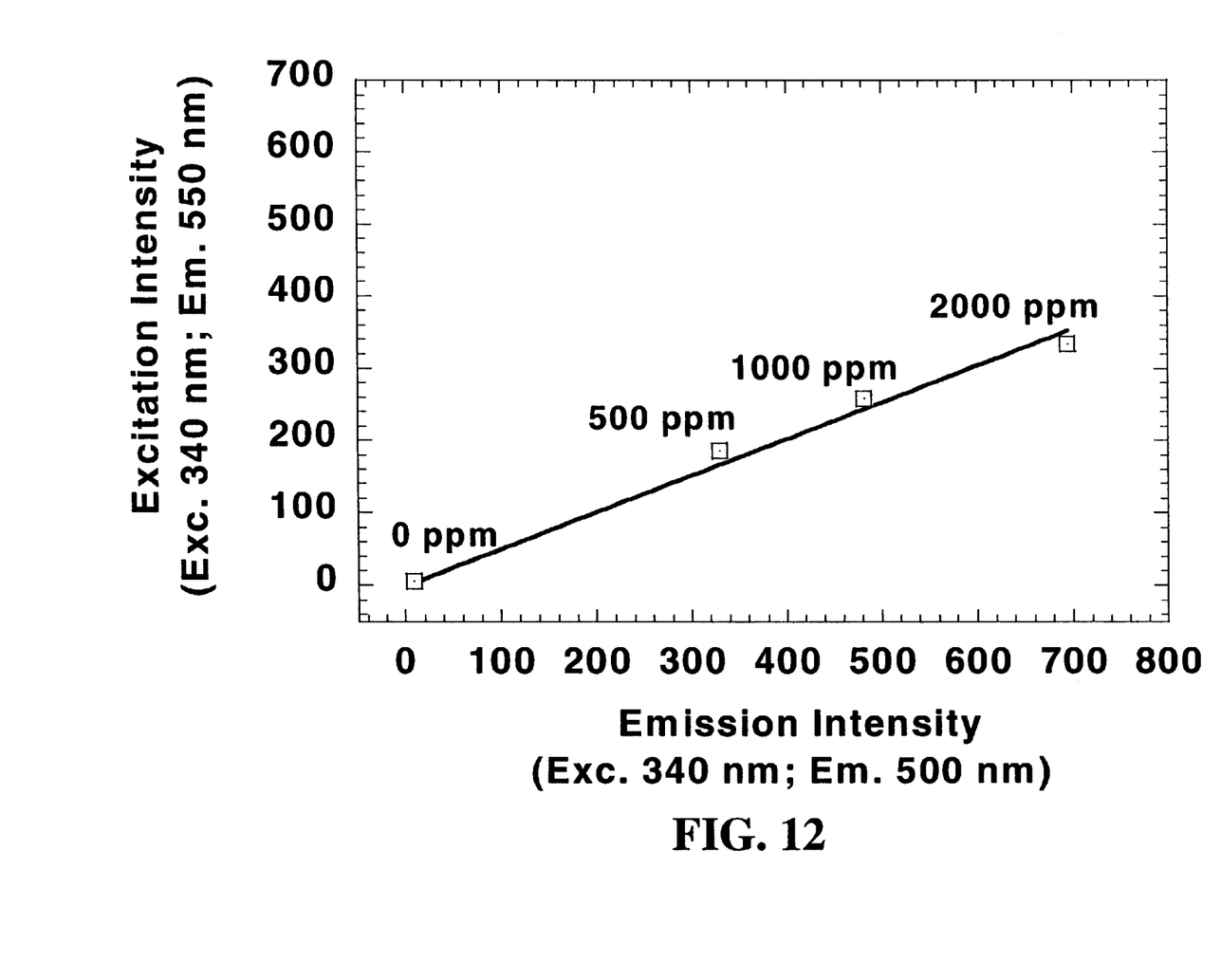
FIG. 12 is a correlation plot of fluorescence intensities of LF polycarbonate at various concentrations of Fries product.

FIG. 12 shows a correlation plot of fluorescence intensities of excitation and emission spectra of the polycarbonate solutions. The horizontal scale represents fluorescence intensity of the emission spectra at 500 nm with a constant excitation wavelength of 340 nm. The vertical scale represents fluorescence intensity of the excitation spectra at 550 nm with a constant excitation wavelength of 340 nm. The strong correlation between the fluorescence intensities of the excitation and emission spectra suggests that a single species (Fries product) contributes to the variation of fluorescence intensity at the selected analytical wavelengths. This theory was verified by performing an NMR end group determination in measured samples. As detailed in TABLE 1 below, the NMR data indicate different amounts of branched Fries and the existence of only negligible amounts of non-branched Fries endgroups.

TABLE 1

| Reacted Fries/ ppm | Non Fries Endgroups/ppm | Fries Endgroups/ ppm (non branched) | Estimated Fries/ ppm (branched) |
| --- | --- | --- | --- |
| 500 | 200 | <20 | 480 |
| 1000 | 210 | <20 | 980 |
| 2000 | 98 | <20 | 1980 |

The data in Table 1 are indicative of variation in the non-Fries endgroups from 98 to 210 ppm. However, it is believed that these interference species do not affect the fluorescence measurements at the selected excitation and emission conditions.

It will be understood that each of the elements described above, or two or more together, may also find utility in applications differing from the types described herein. While the invention has been illustrated and described as embodied in a method for obtaining direct fluorescence measurements from polycarbonate compositions, it is not intended to be limited to the details shown, since various modifications and substitutions can be made without departing in any way from the spirit of the present invention. For example, robotic equipment may be used to prepare the polycarbonate samples and various other types of parallel screening methods may be used in conjunction with the present method. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method of directly determining the concentration of a target species in a composition comprising aromatic carbonate chain units, said method comprising the steps of:
   (a) irradiating a portion of said composition with electromagnetic radiation at an excitation wavelength sufficient to cause said target species to emit a fluorescence spectrum;
   (b) detecting at least a portion of said fluorescence spectrum; and
   (c) determining the concentration of said target species from said fluorescence spectrum.

2. The method of claim 1, wherein said target species is a thermal Fries product.

3. The method of claim 2, wherein said composition is irradiated at an excitation wavelength that allows said Fries product to fluoresce at a detectable level that provides differential emission between said Fries product and interfering species.

4. The method of claim 3, wherein said excitation wavelength is between about 250 nm and about 500 nm.

5. The method of claim 4, wherein said excitation wavelength is between about 300 nm and about 400 nm.

6. The method of claim 5, wherein said excitation wavelength is between about 320 nm and about 350 nm.

7. The method of claim 6, wherein said excitation wavelength is about 340 nm.

8. The method of claim 1, wherein steps (a) and (b) occur during a polycarbonate reaction in a reactor system.

9. The method of claim 8, wherein steps (a) and (b) occur without removing any of said composition from said reactor system.

10. The method of claim 1, wherein steps (a) and (b) occur during a melt polycarbonate reaction.

11. The method of claim 2, wherein steps (a) and (b) occur during a melt polycarbonate reaction.

12. The method of claim 1, wherein said composition is a polycarbonate resin.

13. The method of claim 1, wherein said composition is a polycarbonate blend.

14. The method of claim 1, wherein said composition is in the form of a film.

15. The method of claim 1, wherein said composition is in the form of a sheet.

16. The method of claim 1, wherein said composition is in the form of a pellet.

17. The method of claim 1, wherein said composition is in the form of a solution.

18. A method of determining the concentration of a target species in a composition comprising aromatic carbonate chain units during a polycarbonate reaction, said method comprising the steps of:
   (a) providing a first emission spectrum of said target species containing an initial second order Rayleigh scatter peak;
   (b) exciting said target species with electromagnetic radiation;
   (c) detecting the emission intensity of said target species to provide a second emission spectrum containing another second order Rayleigh scatter peak;
   (d) scaling said first and second spectra such that said second order Rayleigh scatter peaks are the same height; and
   (e) determining the concentration of said target species.

19. The method of claim 18, wherein said target species is a thermal Fries product.

20. The method of claim 18, wherein both emission spectra are obtained during the course of a reaction.

21. The method of claim 19, wherein said composition is excited with electromagnetic radiation at a wavelength that allows said Fries product to fluoresce at a detectable level to provide differential emission between said Fries product and interfering species.

22. The method of claim 21, wherein said excitation wavelength is between about 300 nm and about 400 nm.

23. The method of claim 22, wherein said excitation wavelength is between about 320 nm and about 350 nm.

24. The method of claim 23, wherein said excitation wavelength is about 340 nm.

25. A method of directly determining the concentration of a target species in parallel polycarbonate reactor systems, said method comprising the steps of:

(a) providing a polycarbonate reactor system having multiple reaction zones;

(b) disposing an optical probe proximate each of said multiple reaction zones;

(c) conducting a melt polymerization reaction within each of said multiple reaction zones such that each zone contains a composition comprising aromatic carbonate chain units;

(d) passing electromagnetic radiation through each of said optical probes at an excitation wavelength sufficient to cause said target species to emit a fluorescence spectrum;

(e) detecting at least a portion of said fluorescence spectrum from each of said reaction zones; and (f) determining the concentration of said target species in each of said reaction zones.

26. The method of claim 25, wherein said target species is a thermal Fries product.

27. The method of claim 26, wherein said excitation wavelength is between about 300 nm and about 400 nm.

28. The method of claim 27, wherein said excitation wavelength is between about 320 nm and about 350 nm.

29. The method of claim 28, wherein said excitation wavelength is about 340 nm.

30. A method of directly determining the concentration of a thermal Fries product in a composition comprising aromatic carbonate chain units, said method comprising the steps of:

(a) irradiating a portion of said composition with electromagnetic radiation during a melt polycarbonate reaction at an excitation wavelength between about 320 nm and about 350 nm, to cause said thermal Fries product to emit a fluorescence spectrum;

(b) detecting at least a portion of said fluorescence spectrum during said melt polycarbonate reaction; and (c) determining the concentration of said thermal Fries product from said fluorescence spectrum.

* * * * *